(12) United States Patent
Hsien et al.

(10) Patent No.: US 12,121,430 B1
(45) Date of Patent: Oct. 22, 2024

(54) REUSABLE DIAPER

(71) Applicants: Chi Chen Hsien, Sacramento, CA (US); Thomas C. Chan, Palo Alto, CA (US)

(72) Inventors: Chi Chen Hsien, Sacramento, CA (US); Thomas C. Chan, Palo Alto, CA (US)

( * ) Notice: Subject to any disclaimer, the term of this patent is extended or adjusted under 35 U.S.C. 154(b) by 0 days.

(21) Appl. No.: 18/521,167

(22) Filed: Nov. 28, 2023

(51) Int. Cl.
*A61F 13/495* (2006.01)
*A61F 5/44* (2006.01)
*A61F 13/494* (2006.01)

(52) U.S. Cl.
CPC .......... *A61F 13/495* (2013.01); *A61F 5/4404* (2013.01); *A61F 13/4942* (2013.01)

(58) Field of Classification Search
CPC .................. A61F 13/495; A61F 5/4404; A61F 13/4942
See application file for complete search history.

(56) References Cited

U.S. PATENT DOCUMENTS

| | | | | |
|---|---|---|---|---|
| 5,062,840 A | * | 11/1991 | Holt | A61F 13/495 604/385.19 |
| 5,176,672 A | * | 1/1993 | Bruemmer | A61F 13/495 604/385.19 |
| 5,429,632 A | * | 7/1995 | Tanji | A61F 13/5116 604/394 |
| 5,520,674 A | * | 5/1996 | Lavon | A61F 13/47227 604/385.16 |
| 5,643,241 A | * | 7/1997 | Ahr | A61F 13/495 604/385.12 |
| 6,022,338 A | * | 2/2000 | Putzer | A61F 13/495 604/385.01 |
| 6,090,994 A | * | 7/2000 | Chen | A61F 13/49 604/385.01 |
| 6,093,869 A | * | 7/2000 | Roe | A61F 13/42 604/385.12 |
| 6,133,501 A | * | 10/2000 | Hallock | A61F 13/495 604/385.24 |
| 6,149,636 A | * | 11/2000 | Roe | A61F 13/495 604/385.12 |
| 6,160,198 A | * | 12/2000 | Roe | A61F 13/495 604/385.12 |
| 6,168,584 B1 | * | 1/2001 | Allen | A61F 13/495 604/385.19 |
| 6,328,724 B1 | * | 12/2001 | Ronnberg | A61F 13/49473 604/385.27 |
| 6,346,097 B1 | * | 2/2002 | Blaney | A61F 13/495 604/374 |

(Continued)

*Primary Examiner* — Guy K Townsend
(74) *Attorney, Agent, or Firm* — Silicon Valley Patent Group LLP

(57) ABSTRACT

Apparatuses of reusable diapers and methods for manufacturing the same are provided. In one embodiment, a diaper includes an interior layer includes an excretion area, where the excretion area includes one or more openings configured to drain excretions of a user away from the interior layer, a middle layer configured to house an excretion collection unit, where the excretion collection unit is configured to store the excretions from the interior layer, an exterior layer configured to conceal and prevent leakage from the middle layer of the diaper, and a support frame configured to hold the interior layer, the middle layer and the exterior layer of the diaper together.

20 Claims, 12 Drawing Sheets

(56) References Cited

U.S. PATENT DOCUMENTS

| | | | |
|---|---|---|---|
| 6,372,951 B1* | 4/2002 | Ter-Ovanesyan | A61L 15/26 600/595 |
| 6,383,170 B1* | 5/2002 | Mishima | A61F 13/4942 604/385.27 |
| 6,409,715 B1* | 6/2002 | Tanji | A61F 13/513 604/385.19 |
| 6,458,110 B1* | 10/2002 | Lavon | A61F 13/495 604/385.12 |
| 6,468,256 B1* | 10/2002 | Mishima | A61F 13/495 604/385.03 |
| 6,527,756 B1* | 3/2003 | Mishima | A61F 13/495 604/385.27 |
| 6,565,549 B1* | 5/2003 | Allen | A61F 13/495 604/389 |
| 6,570,053 B2* | 5/2003 | Roe | A61L 15/24 604/362 |
| 6,572,600 B1* | 6/2003 | Roe | A61F 13/5605 604/389 |
| 6,595,972 B1* | 7/2003 | Wise | A61F 13/495 604/385.101 |
| 6,713,660 B1* | 3/2004 | Roe | A61F 13/84 604/367 |
| 6,716,204 B1* | 4/2004 | D'Acchioli | A61F 13/495 604/385.03 |
| 7,160,280 B2* | 1/2007 | Bailey | A61F 13/495 604/385.19 |
| D618,343 S * | 6/2010 | Stephens | D24/124 |
| 7,749,208 B2* | 7/2010 | Moberg-Alehammar | A61F 13/534 604/385.12 |
| 7,927,320 B2* | 4/2011 | Goldwasser | A61F 13/471 604/327 |
| 7,942,859 B2* | 5/2011 | Nakajima | A61F 13/495 604/385.27 |
| 7,982,088 B2* | 7/2011 | Roe | G01N 33/528 604/362 |
| 8,124,828 B2* | 2/2012 | Kline | A61F 13/51464 604/385.101 |
| 8,569,571 B2* | 10/2013 | Kline | A61F 13/539 604/385.101 |
| 8,853,487 B2* | 10/2014 | Takeuchi | A61L 15/42 604/385.01 |
| 8,915,898 B2* | 12/2014 | Dieringer | A61F 13/47236 604/385.19 |
| 10,632,023 B2* | 4/2020 | Kawka | G06N 3/08 |
| 10,786,401 B2* | 9/2020 | Mullane | B32B 3/06 |
| 11,364,158 B2* | 6/2022 | Lee | A61F 13/53717 |
| 11,596,561 B2* | 3/2023 | Hammond | B32B 3/263 |
| 11,771,605 B2* | 10/2023 | Schmoker | A61F 13/53747 604/378 |
| 2002/0019615 A1* | 2/2002 | Roe | A61L 15/26 604/361 |
| 2004/0193130 A1* | 9/2004 | Fima | A61F 13/82 604/385.19 |
| 2008/0004593 A1* | 1/2008 | Lodge | A61F 13/51496 604/401 |
| 2008/0236504 A1* | 10/2008 | Silverman | A01K 1/0107 119/169 |
| 2022/0304866 A1* | 9/2022 | Strasemeier | A61F 13/505 |
| 2023/0363959 A1* | 11/2023 | Kuntze | A61F 13/51113 |

\* cited by examiner

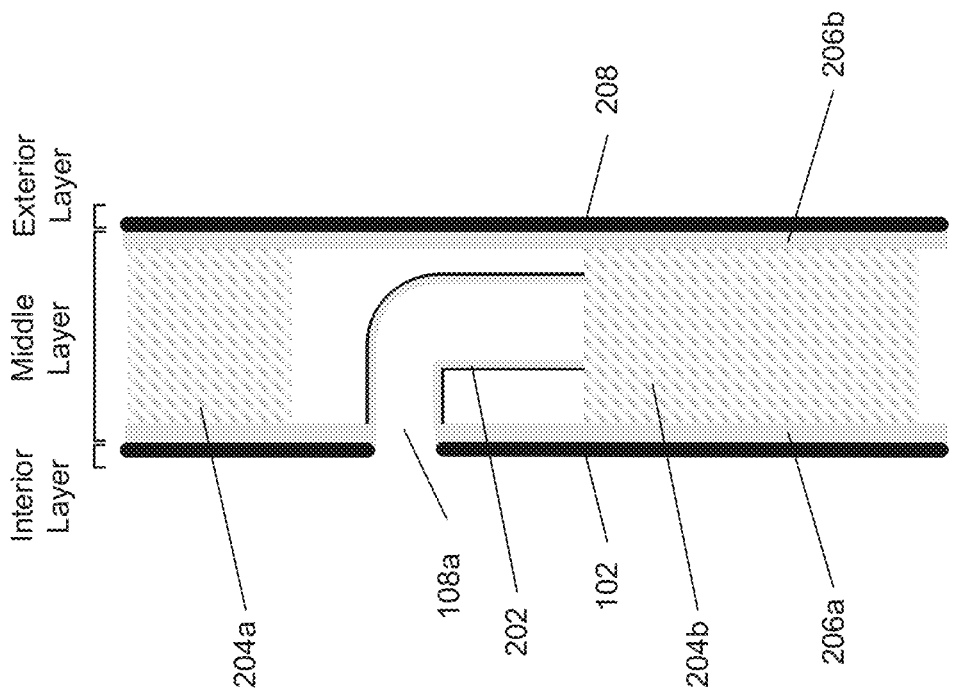
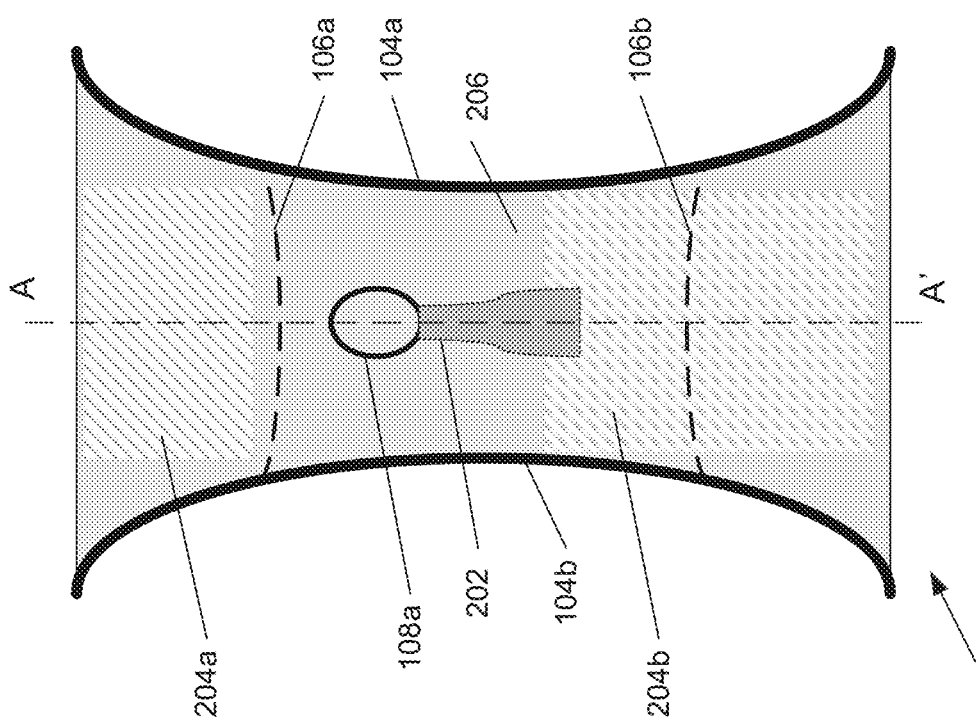
FIG. 2B
FIG. 2A

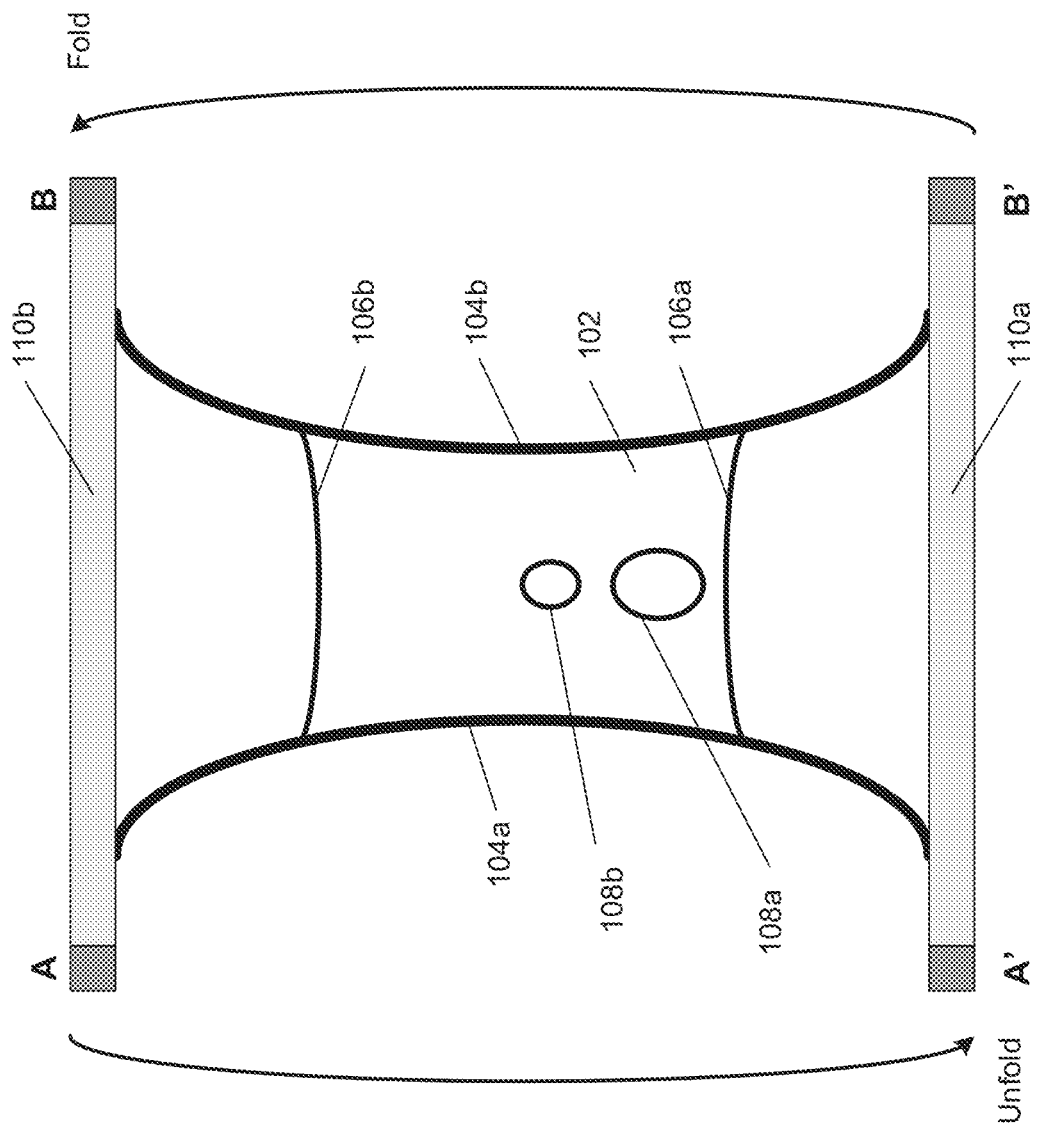

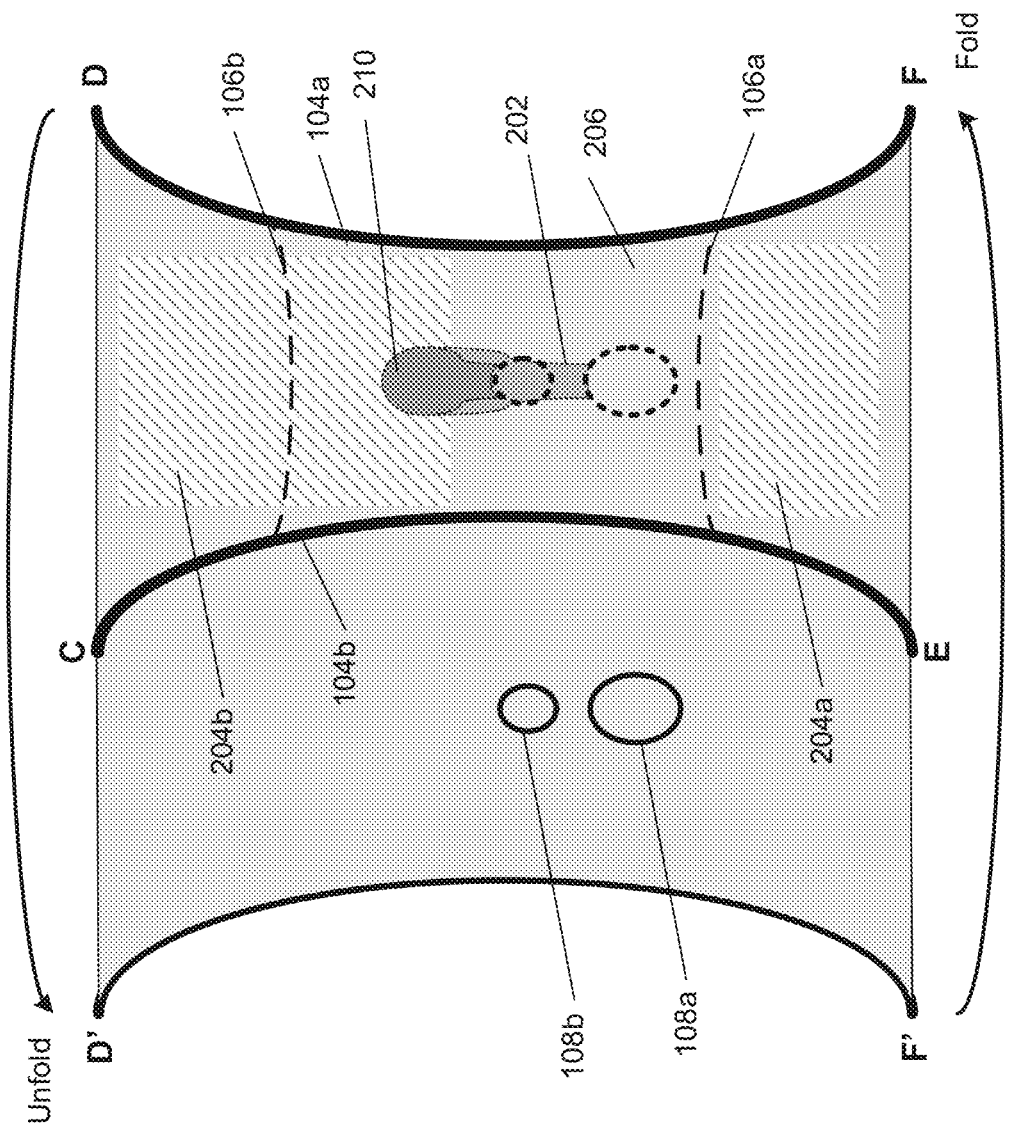

REUSABLE DIAPER

FIELD

The present invention relates to the field of diapers. In particular, the present invention relates to apparatuses of a reusable diaper and methods for manufacturing the same.

BACKGROUND

A diaper is an absorbent item used by babies or adults to defecate and urinate without going to the toilet. The global market for baby disposable diapers is estimated to be US$43.1 Billion in the year 2022. For babies, toddlers, and people lacking voluntary control over urination or defecation who rely on these diapers every day, the quality, safety, performance, and environmentally friendly diapers are paramount. Many types of disposable diapers are readily available commercially. However, the conventional disposable diapers suffer from a number of drawbacks, for example: 1) low absorption rate and long absorption time; 2) skin rashes and stains due to contact with urine/feces for a long time; and 3) producing large amount of non-biodegradable waste materials. Therefore, there is a need for an environmentally-friendly reusable diaper that can address the drawbacks of conventional diapers.

SUMMARY

Apparatuses of reusable diapers and methods for manufacturing the same are provided. In one embodiment, a diaper includes an interior layer includes an excretion area, where the excretion area includes one or more openings configured to drain excretions of a user away from the interior layer, a middle layer configured to house an excretion collection unit, where the excretion collection unit is configured to store the excretions from the interior layer, an exterior layer configured to conceal and prevent leakage from the middle layer of the diaper, and a support frame configured to hold the interior layer, the middle layer and the exterior layer of the diaper together.

In another embodiment, a method of manufacturing a diaper includes forming an interior layer includes an excretion area, where the excretion area includes one or more openings configured to drain excretions of a user away from the interior layer, forming a middle layer configured to house an excretion collection unit, where the excretion collection unit is configured to store the excretions from the interior layer; forming an exterior layer configured to conceal and prevent leakage from the middle layer of the diaper, and forming a support frame configured to hold the interior layer, the middle layer and the exterior layer of the diaper together.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. The drawings are shown for illustration purposes. They are not drawn to scale. Like numbers are used throughout the specification.

FIG. 2A illustrates a top view of a middle layer of the exemplary reusable diaper of FIG. 1A according to aspects of the present disclosure.

FIG. 2B illustrates a cross sectional view of the exemplary reusable diaper of FIG. 1A according to aspects of the present disclosure.

FIG. 3C illustrates an exemplary implementation of fold and unfold operations of the exemplary reusable diaper of FIG. 1B according to aspects of the present disclosure.

FIG. 3D illustrates another exemplary implementation of fold and unfold operations of the exemplary reusable diaper of FIG. 1B according to aspects of the present disclosure.

DESCRIPTION OF EMBODIMENTS

Apparatuses of reusable diapers and methods for manufacturing the same are provided. The following descriptions are presented to enable a person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

Figure 1A:
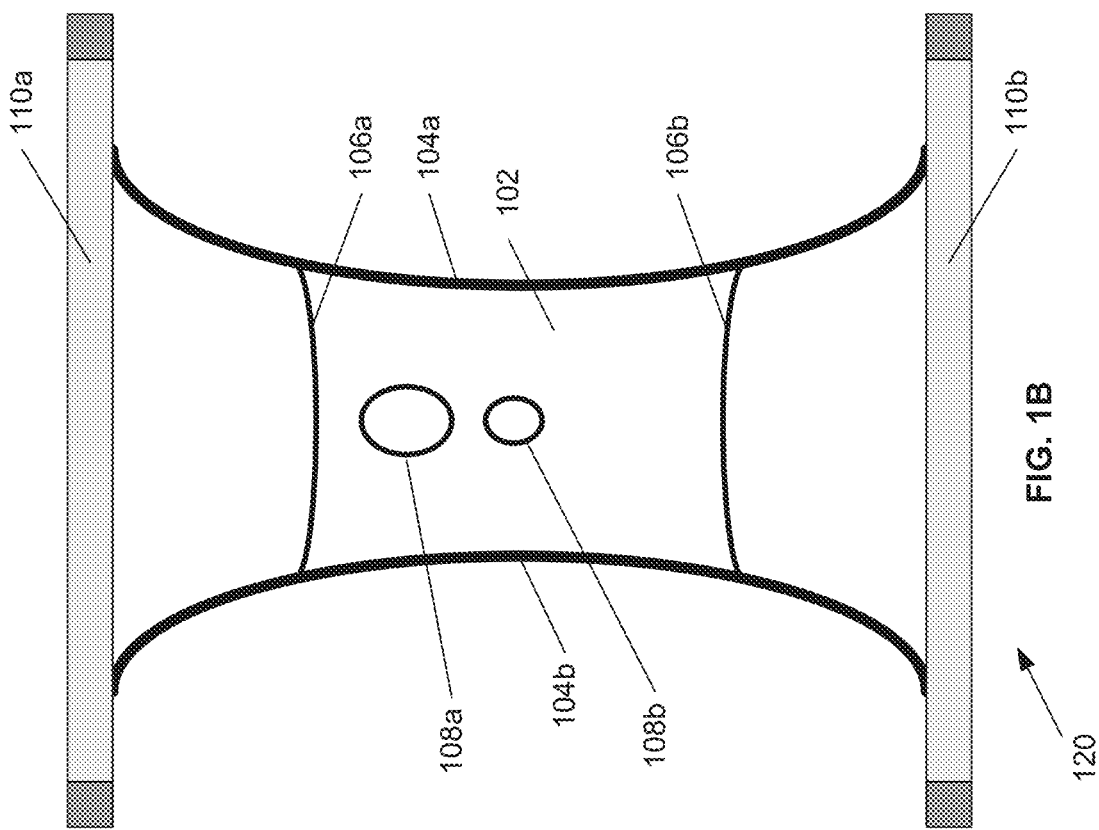
FIG. 1A illustrates a top view of an exemplary reusable diaper according to aspects of the present disclosure.

FIG. 1A illustrates a top view of an exemplary reusable diaper according to aspects of the present disclosure. In the example of FIG. 1A, a reusable diaper 100 includes an interior layer 102 and a support frame, represented by lines 104a and 104b. The interior layer includes an excretion area, outlined within the two curve lines 106a and 106b. The excretion area includes an opening 108a configured to drain excretions of a user away from the interior layer 102. The interior layer 102 is made of a hydrophobic material configured to repel the excretions of the user from the opening 108a to the middle layer of the exemplary reusable diaper. The reusable diaper 100 may further include strapping mechanisms, represented by 110a and 110b, configured to strap the reusable diaper to the body of a user.

According to aspects of the present disclosure, the interior layer 102 can be made of a breathable, stretchable polytetrafluoroethylene treated cotton-spandex waterproof fabric sheet or polytetrafluoroethylene treated nylon-spandex waterproof fabric sheet. The interior layer is attached to the support frame. The upper surface of the interior layer is configured to closely contact with the skin of a user to avoid skin rashes and stains from urine and feces. The lower surface, also referred to as the excretion area, of the interior layer is configured to adhere with the excretion collection unit.

Figure 1B:
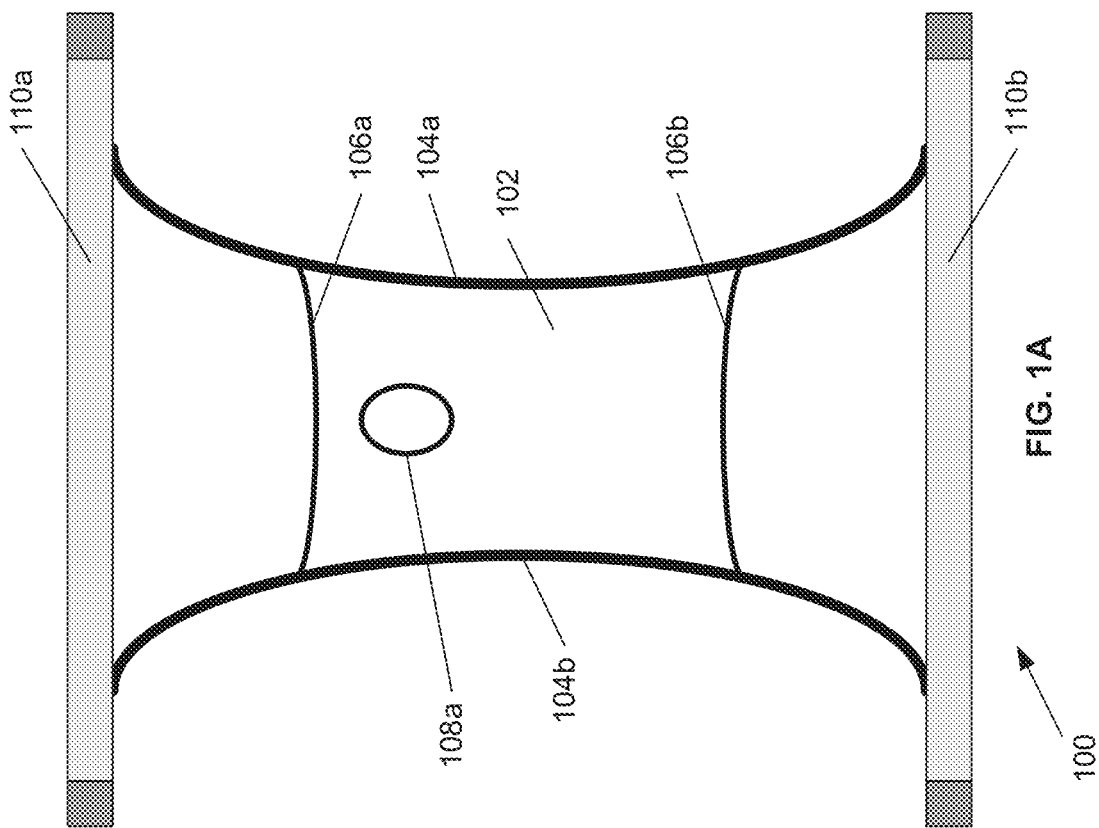
FIG. 1B illustrates a top view of another exemplary reusable diaper according to aspects of the present disclosure.

FIG. 1B illustrates a top view of another exemplary reusable diaper according to aspects of the present disclosure. Some of the components of the reusable diaper 120 are the same as the components shown in FIG. 1A, such as the interior layer 102, the support frame 104a and 104b, and the strapping mechanisms 110a and 110b. The description of similar components are not repeated here. In the example of FIG. 1B, the excretion area includes openings 108a and 108b, configured to drain urine and feces of a user away from the interior layer 102, respectively.

FIG. 2A illustrates a top view of a middle layer of the exemplary reusable diaper of FIG. 1A according to aspects of the present disclosure. Some of the components of the middle layer of the reusable diaper 100 are the same as the components shown in FIG. 1A, such as the support frame 104a and 104b, and the excretion area 106a and 106b. The description of similar components are not repeated here. In the example shown in FIG. 2A, a middle layer 200 is configured to house an excretion collection unit, where the excretion collection unit is configured to store the excretions from the interior layer. The excretion collection unit includes a urine collection unit having a urine guide 202 configured to drain urine away from the interior layer to one or more urine absorbent pads, represented by 204a and 204b in the middle layer 200. The urine collection unit further includes a urine transfer pouch 206 made of a hydrophilic fabric and is configured to accelerate urine absorption by spreading and transferring urine to the one or more urine absorbent pads 204a and 204b.

According to aspects of the present disclosure, a urine guide 202 is used to facilitate transfer of urine away from the genital to the urine transfer pouch 206. The urine guide can be made of a 2 mm thick flexible high density polyethylene sheet. In some applications, the urine guide may drain about 90% to 95% urine output away from the genital during urination. The front portion of the urine guide is adhered to the urinary opening of the interior layer, where the front rim of the urine guide may be in close contact with the interior layer around the genital to prevent urine leakage. Based on the size of the diaper, the size of the urine guide may be 1 cm to 1.2 cm in height and 3 cm to 4 cm in width, configured to provide enough room to cover the genital.

FIG. 2B illustrates a cross sectional view of the exemplary reusable diaper of FIG. 1A according to aspects of the present disclosure. The cross sectional view may be envisioned as a view along line AA' (shown in FIG. 2A) of the exemplary reusable diaper 100. Some of the components of the reusable diaper 100 are the same as the components shown in FIG. 1A and FIG. 2A, such as the urine guide 202, the urine absorbent pads 204a and 204b, the interior layer 102 and the opening 108a. The description of similar components are not repeated here.

As shown in FIG. 2B, a urine transfer pouch, represented by 206a and 206b, is attached to interior layer 102 and exterior layer 208, respectively. The urine transfer pouch is configured to hold the urine collection unit between the interior layer 102 and the exterior layer 208. According to aspects of the present disclosure, the exterior layer 208 is configured to conceal and prevent leakage from the middle layer 200 of the reusable diaper. The exterior layer 208 is made of a breathable material configured to allow moisture from the middle layer to escape the diaper.

In some implementations, the front portion of the urine guide 202 may be attached to the urinary opening of the interior layer configured to contact with the urine transfer pad 206a and urine absorbent pad 204a and the rear portion of the urine guide 202 may be attached to the rear portion of the interior layer configured to contact with the urine transfer pad 206b and urine absorbent pad 204b. The inner surface of the urine guide may be covered with a reusable urine linking pad, which may be made of a 3 mm thick microfiber non-woven fabric configured to use the urine linking pad to link the urine transfer pad 206a and the urine transfer pad 206b together. In addition, a urine guiding film made of a hydrophobic polytetrafluoroethylene may be adhered to the central surface of the reusable urine linking pad, wherein the urine guiding film can further function to guide 90% to 95% of urine output flow away from the genital area and transfer the urine output downward the rear portion of the urine guide configured to absorbed by the urine transfer pad 206b and urine absorbent pad 204b, wherein the remaining 5% to 10% urine output may be absorbed by the urine transfer pad 206a and urine absorbent pad 204a for keeping the genital dry.

Figure 2D:
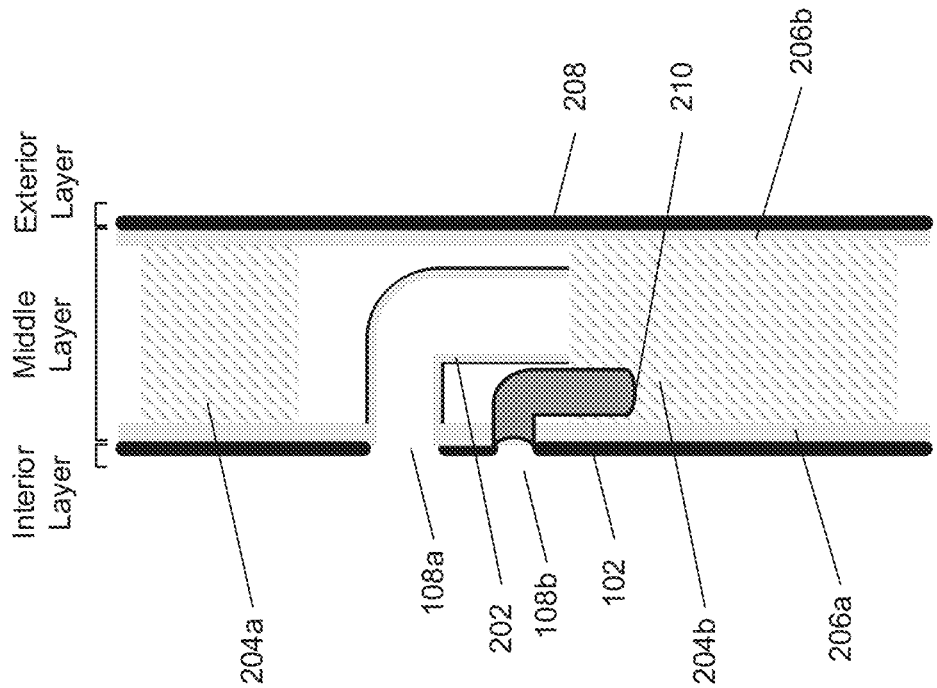
FIG. 2D illustrates a cross sectional view of the exemplary reusable diaper of FIG. 1B according to aspects of the present disclosure.
Figure 2C:
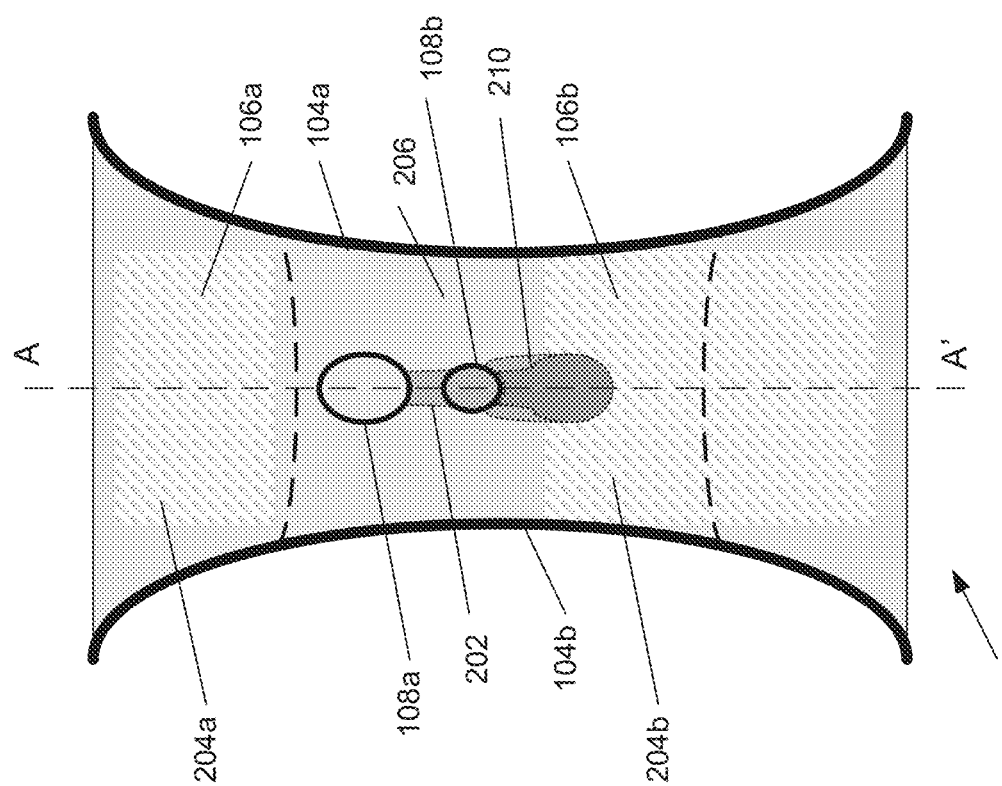
FIG. 2C illustrates a top view of a middle layer of the exemplary reusable diaper of FIG. 1B according to aspects of the present disclosure.

FIG. 2C illustrates a top view of a middle layer of the exemplary reusable diaper of FIG. 1B according to aspects of the present disclosure. Some of the components of the middle layer of the reusable diaper 120 are the same as the components shown in FIG. 2A. The description of similar components are not repeated here. FIG. 2C is similar to the example shown in FIG. 2A with the addition of a feces collection unit. The feces collection unit includes a feces collection bag 210. According to aspects of the present disclosure, the feces collection unit is washable. A used feces collection bag can be replaced with a new feces collection bag.

In some implementations, the feces collection unit may optionally and/or additionally include a barrier anus shield with air cushion rectum seat. The barrier anus shield may be made of thermoplastic elastomers or polydimethylsiloxane rubber sheet with a dimension of 3 cm to 4 cm in width, 1 to 2 mm in thickness and 5 cm to 6 cm in length. The barrier anus shield may be attached to the fecal drain opening of the interior layer as well as to the support frame.

The barrier anus shield includes a ring shaped air cushion rectum seat bonded on the top of a feces drain opening which is located at the central portion of the barrier anus shield. The air cushion rectum seat may be snug fitted to the rim of the rectum, allowing collection of feces easily. The feces collection bag may be detachable from the rectum air cushion seat, allowing changing or disposing of a used feces collection bag. The feces collection bag of the present disclosure is distinguished from the conventional diapers. With conventional diapers, collect feces directly on the inner layer of the diaper, which may cause feces to stain the skin or genital of the user, which may in turn cause rashes to the skin or genital of the user.

FIG. 2D illustrates a cross sectional view of the exemplary reusable diaper of FIG. 1B according to aspects of the present disclosure. The cross sectional view may be envisioned as a view along line AA' (shown in FIG. 2C) of the exemplary reusable diaper 220. Some of the components of the middle layer of the reusable diaper 220 are the same as the components shown in FIG. 2B and FIG. 2C. The description of similar components are not repeated here.

According to aspects of the present disclosure, the exterior layer 208 may be made of a stretchable, breathable, washable polytetrafluoroethylene treated cotton-spandex waterproof fabric sheet or polytetrafluoroethylene treated nylon-spandex waterproof fabric sheet. In some implementations, the urine transfer pouch can be made of a hydrophilic wicking material, such as hydrophilic microfiber non-woven fabric.

The urine transfer pouch includes a front double layer microfiber pad, a reusable urine linking pad and a rear double layer microfiber pad. The front and the rear double layer microfiber pads can be made of one piece of 6 cm×28 cm×2 mm microfiber non-woven fabric sheet, which can be folded to form a 6 cm×14 cm×4 mm double layer microfiber pad. The top layer of the double layer microfiber pad (from perspective when diaper is worn) can be adhered to the interior layer of the diaper, and the outside layer of the double layer microfiber pad can be adhered to the exterior layer of the diaper.

Figure 3B:
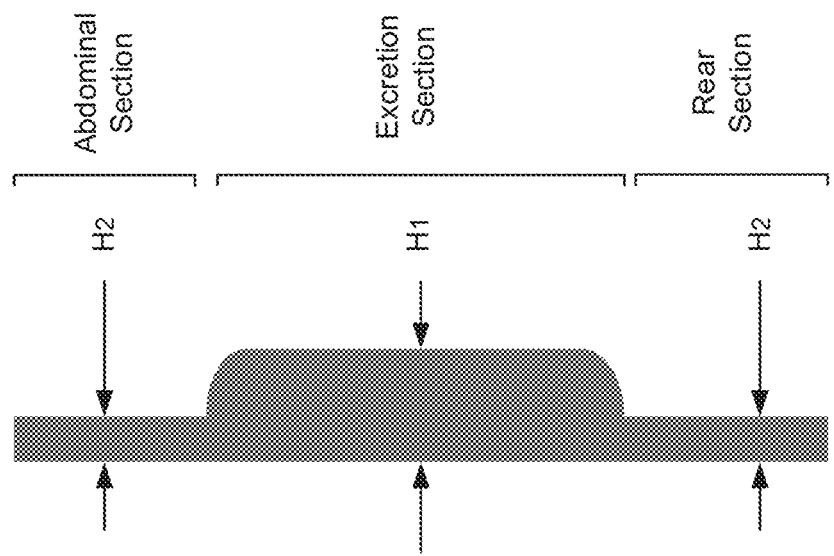
FIG. 3B illustrates a side view of the support frame of FIG. 3A according to aspects of the present disclosure.
Figure 3A:
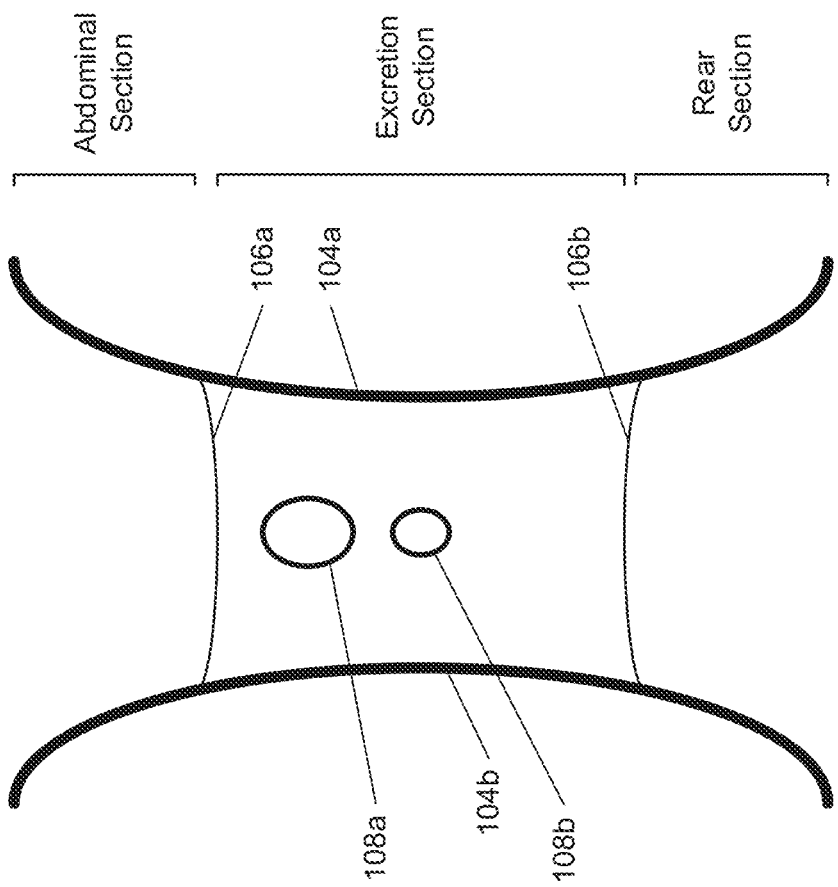
FIG. 3A illustrates a top view of an exemplary implementation of a support frame of the exemplary reusable diaper of FIG. 1A according to aspects of the present disclosure.

FIG. 3A illustrates a top view of an exemplary implementation of a support frame of the exemplary reusable diaper of FIG. 1A according to aspects of the present disclosure. Some of the components shown in FIG. 3A are the same as the components shown in FIG. 1A. The description of similar components are not repeated here. As shown in the example of FIG. 3A, the support frame includes an excretion section located around the genital area of the user configured to hold the excretion collection unit, an abdominal section of the support frame located at a front portion of the crotch area configured to hold the diaper that touches an abdominal area of the user, and a rear section of the support frame located at a back portion of the crotch area configured to hold the diaper that touches a rear area of the user.

According to aspects of the present disclosure, the support frame is configured to hold the interior layer, the middle layer and the exterior layer of the diaper together. The support frame is made of hydrophobic polydimethylsiloxane rubber or thermoplastic elastomers, and is configured to wrap around the crotch area of the user to prevent leakage.

FIG. 3B illustrates a side view of the support frame of FIG. 3A according to aspects of the present disclosure. As shown in FIG. 3B, the support frame in the excretion section and the rear section have a height of $H_1$. The height of $H_1$ depends on different sizes for different users, which may have a range of 1.2 to 1.5 centimeters. The support frame in the abdominal section has a height of $H_2$. The height of $H_2$ depends on different sizes for different users, which may have a range of 0.8 to 1.2 centimeters.

According to aspects of the present disclosure, the increased height of the support frame in the excretion area is designed to seal the diaper to the crotch area of the user and to provide an air gap between the excretion area of the interior layer of the diaper and a genital area of the user. The air gap reduces or prevents feces from touching the skin of the user. The height of the support frame in the abdominal section is designed to have a lower height than the excretion area to minimize bulging, which allows a close snug to the skin of the user in the abdominal and rear areas of the diaper.

According to aspects of the present disclosure, the support frame is configured to fold or unfold in a first direction to provide access to the excretion collection unit in the middle layer of the diaper, and where the support frame is further configured to fold or unfold in a second direction to wrap or unwrap the diaper around the crotch area of the user.

FIG. 3C illustrates an exemplary implementation of fold and unfold operations of the exemplary reusable diaper of FIG. 1B according to aspects of the present disclosure. The fold and unfold operations are performed by closing and opening the diaper by moving the strapping mechanism 110a with point A and point B at each end, and the strapping mechanism 110b with point A' and point B' at each end.

In FIG. 3C, the diaper is shown in an unfold position, ready to be worn by a user. The diaper may be folded by attaching point A' to point A and point B' to point B. On the other hand, the diaper may be unfolded by detaching point A' from point A and point B' from point B. According to aspects of the present disclosure, the strapping mechanism may be implemented by various means, for example using magnetic strips, adhesive strips, Velcro strips, and etc.

FIG. 3D illustrates another exemplary implementation of fold and unfold operations of the exemplary reusable diaper of FIG. 1B according to aspects of the present disclosure. Some of the components shown in FIG. 3A are the same as the components shown in FIG. 1B, FIG. 2C and FIG. 2D. The description of similar components are not repeated here.

As shown in FIG. 3D, the support frame may be folded and unfolded to provide access to the middle layer of the reusable diaper for cleaning or changing the urine absorbent pads. In this exemplary implementation, the support frame on the right hand side of the diaper may be configured to be detachable along the curve line DF. In the unfold form, a first portion of the support frame 104a remains along the curve line DF, while a second portion of the support frame 104a is moved to the curve line D'F'. In the unfold form, the urine absorbent pads 204a and 204b may be changed; the urine collection unit 202 and the feces collection unit 210 may be replaced; and the middle layer of the diaper may be cleaned. After accessing the middle layer, the diaper may be folded by attaching the first portion and the second portion of the support frame 104a together, i.e. curve D'F' is folded back to curve DF.

Note the directions of the fold and unfold operations in FIG. 3D are shown for illustration purposes. In other embodiments, the support frame 104b may be configured to be detachable along the curve line CE (not shown). According to aspects of the present disclosure, the folding and unfolding mechanism may be implemented by various means, for example using magnetic strips, adhesive strips, Velcro strips, and etc.

In some implementations, the top layer of the front double layer microfiber pad can be adhered on the inner surface of the interior layer in the abdomen portion, where one or more pieces of urine absorbent pads 204a can be placed on the inner surface of the top layer of the front double layer microfiber pad. The bottom layer of the front double layer microfiber pad can be adhered on the exterior layer. When the exterior layer is folded horizontally, the inner layer of the diaper can be configured to hold the urine absorbent pad 204a, which is sandwiched between the top layer and the bottom layer of the front urine transfer pouch. In addition, when the exterior layer is unfolded from the inner layer of the diaper to open the front double layer microfiber pad, access is provided to the reusable components of the diaper, and allows used urine absorbent pads to be changed.

Similarly, the top layer of the rear double layer microfiber pad can be adhered on the inner surface of the interior layer in the top buttocks portion and the bottom layer of the rear double layer microfiber pad can be adhered on the inner surface of the exterior layer, where one or more pieces of urine absorbent pad 204b can be placed on the surface of the inner layer. When the exterior layer is folded horizontally, the interior layer of the diaper can be configured to hold the urine absorbent pad 204b, which is sandwiched between the top layer and the bottom layer of the rear double layer microfiber pad. In addition, when the exterior layer is unfolded horizontally from the inner layer of the diaper to open the rear double layer microfiber pad, access is provided to the reusable components of the diaper, and allows used urine absorbent pads to be changed.

In some implementations the urine absorbent pad includes a muffin pan shaped superabsorbent polymer (SAP) holder which is made of paper pulp by mixing 0.5 weight % to 1.2 weight % of biodegradable hydrophilic carboxymethyl cellulose (CMC), 20 weight % to 30 weight % of hardwood and softwood blend fibers, 2 weight % to 3 weight % of room temperature water soluble polyvinyl alcohol and water into paper pulp and then hot press pulp into muffin pan shaped SAP holder and carboxymethyl cellulose paper sheet. The addition of CMC into paper pulp can increase the dry and wet strength, wicking and absorbance properties of the SAP holder for making a urine absorbent pad. The muffin pan shaped SAP holder may have 6 to 20 collection cups to uniformly distribute the superabsorbent particles into each collection cup of the urine absorbent pad, for example having 6×1, 6×2, 10×1 and 10×2 configurations. In the example of 6×1 configuration, the urine absorbent pad having a size of 13 cm×2.5 cm×1 cm may contain 2 grams to 3 grams of superabsorbent polymer particles.

Figure 4B:
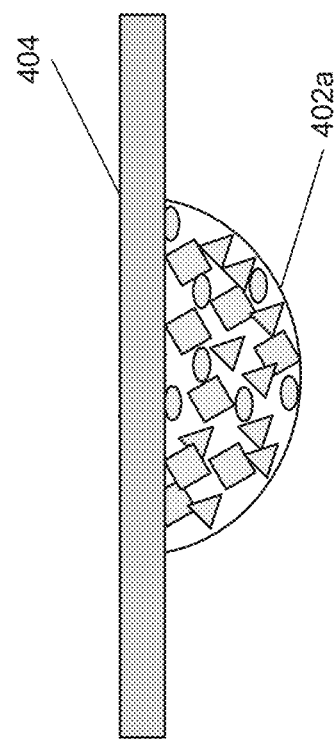
FIG. 4B illustrates an exemplary implementation of a collection cup of the urine absorbent pad of FIG. 4A according to aspects of the present disclosure.
Figure 4A:
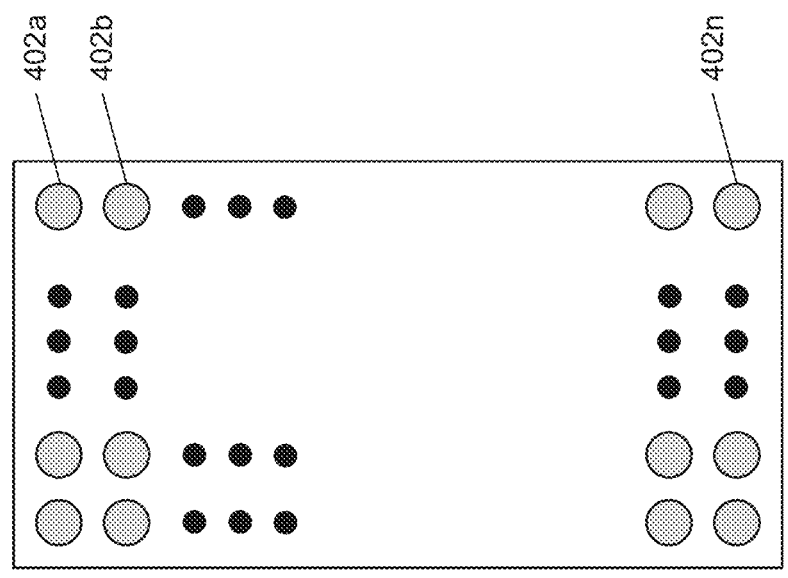
FIG. 4A illustrates an exemplary implementation of a urine absorbent pad according to aspects of the present disclosure.

FIG. 4A illustrates an exemplary implementation of a urine absorbent pad according to aspects of the present disclosure. FIG. 4B illustrates an exemplary implementation of a collection cup of the urine absorbent pad of FIG. 4A according to aspects of the present disclosure. In this exemplary implementation, a urine absorbent pad 400 may include a group of collection cups (represented by 402a, 402b . . . 402n, etc.) connected with a carboxymethyl cellulose (CMC) paper sheet 404. Each cup, for example 402a, in the group of collection cups can be configured to hold biodegradable superabsorbent polymer particles and toilet paper scraps for absorbing urine from the user.

According to aspects of the present disclosure, a used urine absorbent pad is flushable in a toilet. Based on the size of the user and other application criteria, various sizes of urine absorbent pad may be designed. In one implementation, a urine absorbent pad having a rectangular shape of approximately 2 cm to 3 cm in width and 10 cm to 14 cm in length may be used to fit the drainage of a toilet. In some embodiments, a reusable diaper may be designed to hold multiple urine absorbent pads for situations where it is desirable to prolong the period of changing the diaper and/or changing the urine absorbent pads.

The urine absorbent pad is designed with the following features, including but not limited to: 1) use a flushable, dispersible and biodegradable CMC paper; 2) supported by the urine transfer pouch and the support frame to provide space for the superabsorbent polymer particles to undergo free swelling process in order to maximize urine absorption capacity; 3) provide a uniform distribution of 2 grams to 3 grams biodegradable super absorbent polymer particles in the group of collection cups of the urine absorbent pad; 4) use two or more urine absorbent pads in the urine collection unit for an extended period of time (for example overnight) without changing the urine absorbent pads; 5) sandwich the urine absorbent pads between the top layer and the bottom layer of the microfiber pads of the urine transfer pouch to provide tensile strength; and 6) enable a used urine absorbent pad to disintegrate in toilet water.

According to aspects of the present disclosure, the urine absorbent pad uses collection cups to achieve desirable urine swelling rate and swelling capacity. One advantage of the disclosed urine absorbent pad is that it can be disintegrated in water, allowing used urine absorbent pad to be flushed in a toilet. In some implementations, based on the size and intended duration of use of the diaper, the main structure of a urine absorbent pad may include 6 to 20 or more collection cups as the SAP particles holder, for example in 6×1, 6×2, 10×1 and 10×2 configurations. In the example of the 6×1 configuration, the urine absorbent pad may have a dimension of 13 cm×2.5 cm×1 cm, where the 6 collection cups may be made by mixing appropriate proportions of CMC powder, wood fibers and room temperature water-soluble polyvinyl alcohol into pulp and hot-press pulp into a urine absorbent pad with 6 collection cups.

In some implementations, depending on the size and intended duration of use of the diaper, each cup may have a dimension 2 cm×2.2 cm×1 cm with a volume of about 4.4 milliliter (ml) and with a total volume of about 26.4 ml and a thin mesh shape flushable CMC paper sheet as the cover of the cup.

Each cup can be filled with a mixture of two ply toilet paper scraps and about 200 mg to 400 mg of biodegradable superabsorbent polymer particles, and then the water-soluble pressure-sensitive adhesive is used to seal the cups with the flushable CMC paper cover to form a 13 cm×2.5 cm×1 cm urine absorbent pad. This method of mixing the biodegradable superabsorbent polymer particles with the two ply toilet paper scraps is to use toilet paper to absorb urine, and to provide the biodegradable superabsorbent particles having time to absorb urine and dry out the toilet paper for the next round of urine absorption. The collection cups are configured to provide room required for the expansion of wetted biodegradable superabsorbent polymer particles. The biodegradable superabsorbent polymer particles in the urine absorbent pad are under free swelling to have an optimal urine absorption capacity, which in turn keeps the genital area drying and prevents rashes to the skin of the user. In some other implementations, several of the urine absorbent pads may be used together according to the actual urine absorption needs or desired duration between diaper changes.

For example one 6×2 configuration urine absorbent napkin may include two parallel pieces of 13 cm×2.5 cm×1 cm urine absorbent pads, which may be formed on the top surface of a room temperature water-soluble polyvinyl alcohol film, then a water soluble polyvinyl alcohol pressure sensitive adhesive may be used to bond two parallel pieces of 13 cm× 2.5 cm×1 cm urine absorbent pads together to form a 13 cm×5 cm×1 cm urine absorbent napkin.

Based on experimental data, a normal urine output of a user may depend on age, weight, and health. An average urine output can be about 1.5 ml per kilogram (kg) of body weight per hour. For example, a toddler who weighs about 12 kg may have a urine output of about 36 ml in a duration of 2 hours (1.5×12 kg×2 hours=36 ml). According to the experimental results of one commercial SAP sample, the absorption under load (AUL) equilibrium absorption capacity of SAP in the saline solution is about 19.04 ml urine/g SAP. Thus, it may need about 1.9 grams of SAP particles (36 ml/19.04 ml/g SAP=1.9 grams) to absorb 36 ml of urine output. An exemplary implementation of the disclosed diaper contains 2 grams of SAP.

Figure 4C:
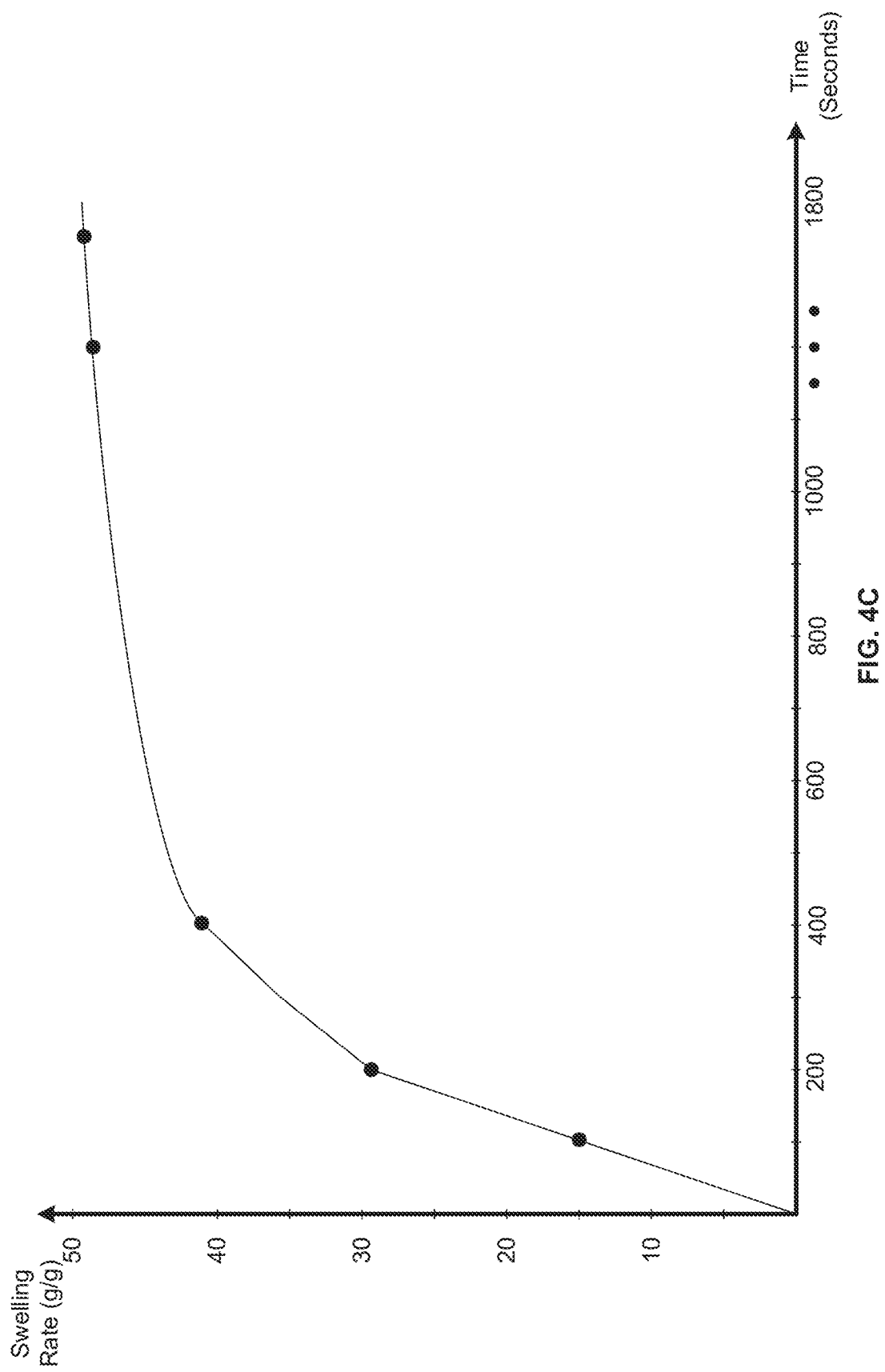
FIG. 4C illustrates an exemplary graphical representation of the swelling rate of superabsorbent polymer particles in a urine solution according to aspects of the present disclosure.

The kinetics of the superabsorbent polymer (SAP) swelling process can be used to analyze how long it should take for a diaper to absorb this 36 ml of urine output. The kinetics of the SAP swelling can be described mathematically using empirical models, such as Voigt viscoelasticity model. FIG. 4C illustrates an exemplary graphical representation of the swelling rate of superabsorbent polymer particles in a urine solution according to aspects of the present disclosure. In the example of FIG. 4C, the swelling rate (also referred to as absorption rate) of a commercial SAP particles sample in a synthetic urine solution (NaCl 0.9 weight % or 0.279 mole %) under free swelling condition without loading pressure as a function of time can be expressed by the Voigt equation:

$$A_t = A\infty(1-\exp(-t/T))$$

where $A_t$ represents (g/g) absorption at time t; $A\infty$ (g/g) represents the power parameter (g urine/g SAP), indicating the theoretical equilibrium of urine absorption; t (s) represents absorption time; and T (s) is the rate parameter, representing the retardation time required to reach 0.632 of equilibrium urine absorption.

As shown in FIG. 4C, the superabsorbent polymer particles absorbed saline solution at a higher rate in the initial 5 minutes, reached a swelling equilibrium in about 15 minutes. Because of this phenomenon, the analysis of the SAP swelling process can be focused on the investigation of initial swelling rate to study the linear relationship of swelling capacity versus time when the swelling is below 60%. The Voigt-based swelling kinetic model may analyze the results of the free swelling capacity (FSC) and absorption under load (AUL) at 0.3 psi of the superabsorbent polymer in 0.9 weight % saline solution (synthetic urine solution).

Figure 4D:
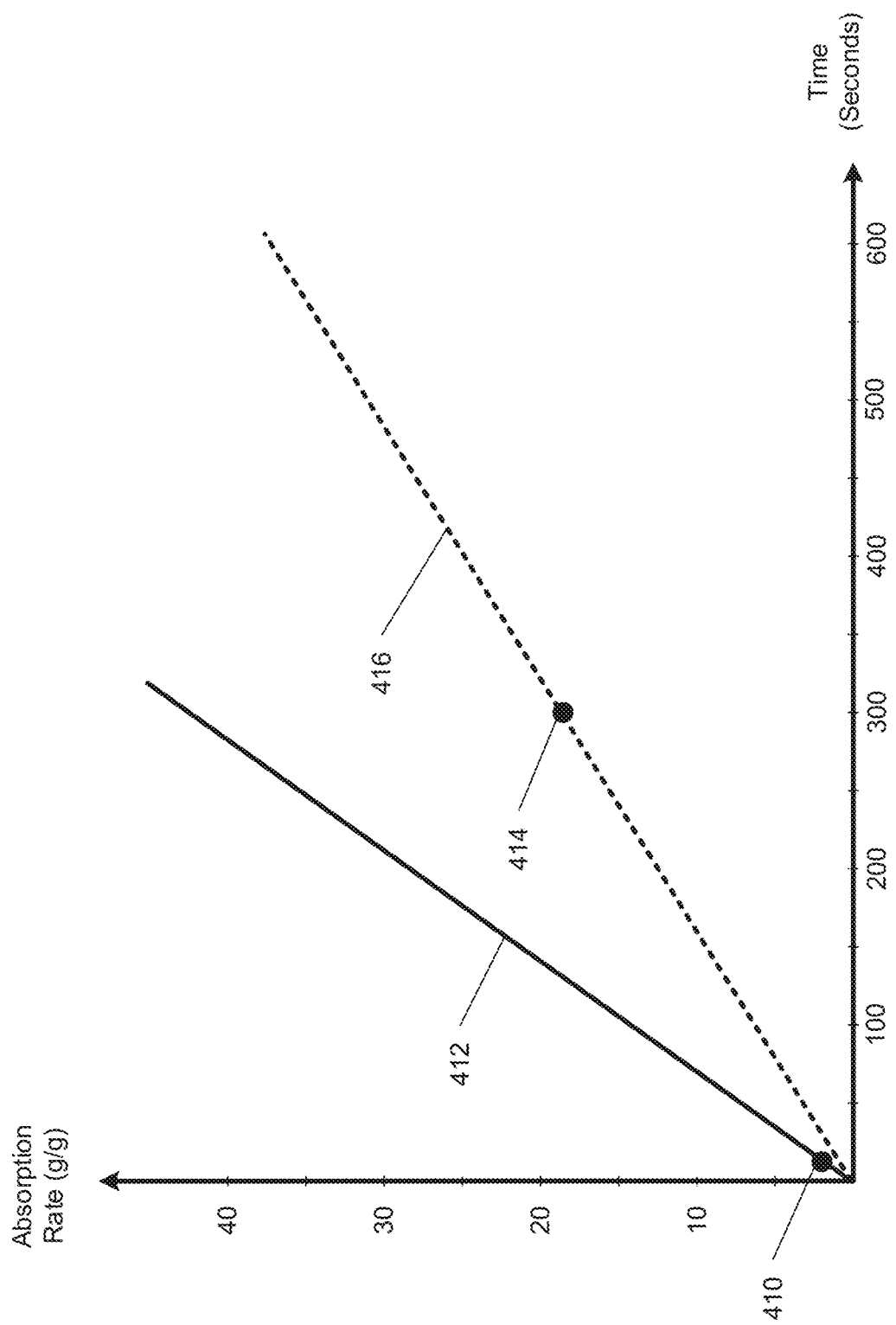
FIG. 4D illustrates a comparison of urine absorption performance of the disclosed reusable diaper based on free swelling capacity to a conventional diaper based on absorption under load of super absorbent polymer particles according to aspects of the present disclosure.

FIG. 4D illustrates a comparison of urine absorption performance of the disclosed reusable diaper based on free swelling capacity to a conventional diaper based on absorption under load (AUL) of super absorbent polymer particles according to aspects of the present disclosure. Case 1: Free swell capacity (FSC, also referred to as free absorption rate) of a commercial superabsorbent polymer sample in 0.9 weight % saline solution (used for the disclosed reusable diaper). The values of $A\infty$ and T can be determined using:

$A\infty$ (g/g)=approximately 47 g saline solution/g SAP at t=1000 sec $A_t$ (g/g)=0.632 $A\infty$
=29.7 g saline solution/g SAP at t=200 sec=T
$A_t$ vs absorption time: linear relation
$dA_t/dt$=29.7/200=0.148 g/g SAP sec
=0.148 ml/g SAP sec (slope)

Using the disclosed urine guide, 90% of 36 ml urine output will be drained away from the genital during urination, leaving about 3.6 ml of urine may remain in the urine guide to be absorbed by the urine absorbent pad. The urine absorbent pad contains 2 grams of SAP particles, which means 1 gram of SAP is used to absorb 1.8 ml of urine.

time=1.8 ml/0.148 ml/1 g×sec=12 sec

Thus, it would take about 12 seconds, represented by dot 410, to absorb the 3.6 ml of urine which is trapped in the urine transfer pouch, shown as solid line 412 in FIG. 4D, for drying the genital area.

Case 2: Absorption under Load (AUL) by the conventional diaper at 0.3 psi using the same superabsorbent polymer sample in 0.9 weight % saline solution:

$A\infty$ (g/g)=19.04 g saline solution/g SAP
A (g/g)=0.632 $A\infty$
=12.1 g saline solution/g SAP at t=200 sec=T
$A_t$ vs sorption time: linear relation
$dA_t/dt$=12.1/200=0.06 ml urine/g SAP/sec (slope)

In the case of a conventional diaper containing 2 grams of SAP particles, 1 gram of SAP would need to absorb 18 ml of urine.

time=18 ml/0.06 ml/1 g×sec=300 sec

Thus, the conventional diaper would need 300 seconds, represented by dot 414, to absorb the 36 ml of urine output, shown as dotted line 416 in FIG. 4D, for drying the genital area.

According to aspects of the present disclosure, the improved urine absorption mechanism of the disclosed reusable diaper can be achieved through the design of the support frame, the urine guide, the urine transfer pouch, and the urine absorbent pads. First, the support frame is made of a flexible polydimethylsiloxane which is resistant to body fluids and can be washed with 70% to 80% ethanol to sterilize the support frame. The support frame has a compressive strength range from 28.4 to 51.7 GPa, enabling it to support the urine transfer pouch and urine absorbent pads without experiencing external pressure. As a result, it functions to prevent diaper rewet and diaper rash.

The urine guide is designed to drain about 90% to 95% urine output away from the genital to the urine transfer pouch and the urine absorbent pad during urination. This enables the disclosed reusable diaper to absorb a typical amount of urine output in significantly less time than a conventional diaper as discussed above.

The urine transfer pouch is designed to hold the urine output during urination and then wick the urine away from the urine transfer pouch to the urine absorbent pads, giving SAP particles in the urine absorbent pads time to absorb a user's urine output held by the urine transfer pouch. After the urine transfer pouch is dried by the urine absorbent pads, it is ready to catch the subsequent cycles of urination. By selecting a moisture wicking fabric to make the urine transfer pouch, urine can be drawn away from the genital area of the user.

According to aspects of the present disclosure, microfiber used in the urine transfer pouch can provide desired absorbency due to greater surface area available to absorb urine and moisture. For example, a 70% polyester/30% polyamide blend 300 GSM microfiber that is capable of absorbing 7 or more times of its weight in liquid can be used. In addition, the initial absorption speed of a microfiber fabric can be shown that the absorption speed of a 5 inches by 5 inches microfiber sample can be completely saturated with water in less than five seconds. For these reasons, the disclosed diaper uses microfiber to make the urine transfer pouch.

In an exemplary implementation, the urine transfer pouch can be made using a micro fiber such as a 3 mm thick 70% polyester/30% polyamide 300 GSM microfiber pad. The total surface area of the urine transfer pouch can be around 392 square cm, which includes the surface area of the front double layer microfiber pad is about of 168 square cm (2×14 cm×6 cm); the surface area of the urine linking pad in the urine guide is about of 56 cm² (11 cm×4 cm+10 cm×0.6 cm×2=56 cm²); and the surface area of the rear double layer microfiber pad is about of 168 square cm (2×14 cm×6 cm), The weight of the urine transfer pouch can be about of 11.76 grams (392 cm²×300 g/m²=11.76 gram). Water absorption capacity of microfiber is approximately 7 ml/g in 4 second, which means that the urine transfer pouch has the capacity to absorb 82.32 ml of urine in about 4 second (11.76 gram×7 ml/g=82.32 ml). Therefore, the urine transfer pouch can hold all of the 36 ml of a typical user's urine output, which in turn enables the urine transfer pouch to have the capability to keep the genital area of the user dry a few seconds after urination.

The urine absorbent pad is formed with a group of uniformly distributed collection cups, where each cup may contain 200 to 400 mg of superabsorbent polymer (SAP) particles. The collection cups provide room for expansion when superabsorbent polymer particles get in contact with urine to undergo free swelling. As shown in FIG. 4C, for free swelling capacity 1 gram of SAP particles may absorb 47 ml of urine. In one implementation, one piece of urine absorbent pad 13 cm×2.5 cm×1 cm containing 3 grams of SAP particles may have a urine absorption capacity of 141 ml. This capability can extend the period of changing the disclosed reusable diaper to 8 hours, such as overnight, for example.

However, in conventional diapers, the stiff fiber matrix can create a compressive force, for example as much as 0.3 psi on the superabsorbent polymer particles. This compressive force causes the superabsorbent polymer particles to undergo an absorption under load (AUL) swelling process, which in turn reduces urine absorption capacity of the conventional diapers.

On the other hand, in some implementations of the reusable diaper, 90% to 95% of the urine output may be drained by the urine guide during urination to the rear double layer microfiber pad. That is, about 32 ml to 34 ml urine (90% to 95% of 36 ml in 2 hours during) may be drained by the urine guide to the rear double layer microfiber pad made of 300 GMS microfiber which has a surface area of about 168 cm² (14 cm×6 cm×2 layers=168 cm²; dimension of pad 14 cm×6 cm×4 mm) and it weighs about 3.36 grams (168 cm²×300 g/m²=5 gram). The water absorption capacity of the rear double layer microfiber is about 7 ml/g in 4 seconds. This means that the rear double layer microfiber pad has the capacity to hold 35 ml of urine in 4 seconds (the water absorption capacity of microfiber 7 ml/g in 4 seconds; 5 gram×7 ml/g microfiber=35 ml) so it has absorbent capacity to hold this 32 to 34 ml of urine output.

The urine linking pad possesses wicking properties to transfer collected urine from the rear double layer microfiber pad to the front double layer microfiber pad, or vice versa. Together, the rear and the front double layer pads share the load of holding 32 to 34 ml of urine. Both the rear and the front double layer pads can be dried out by the urine absorbent pads within minutes, therefore the urine transfer pouch may be used repeatedly to absorb urine output next time when the user urinates.

Figure 5A:
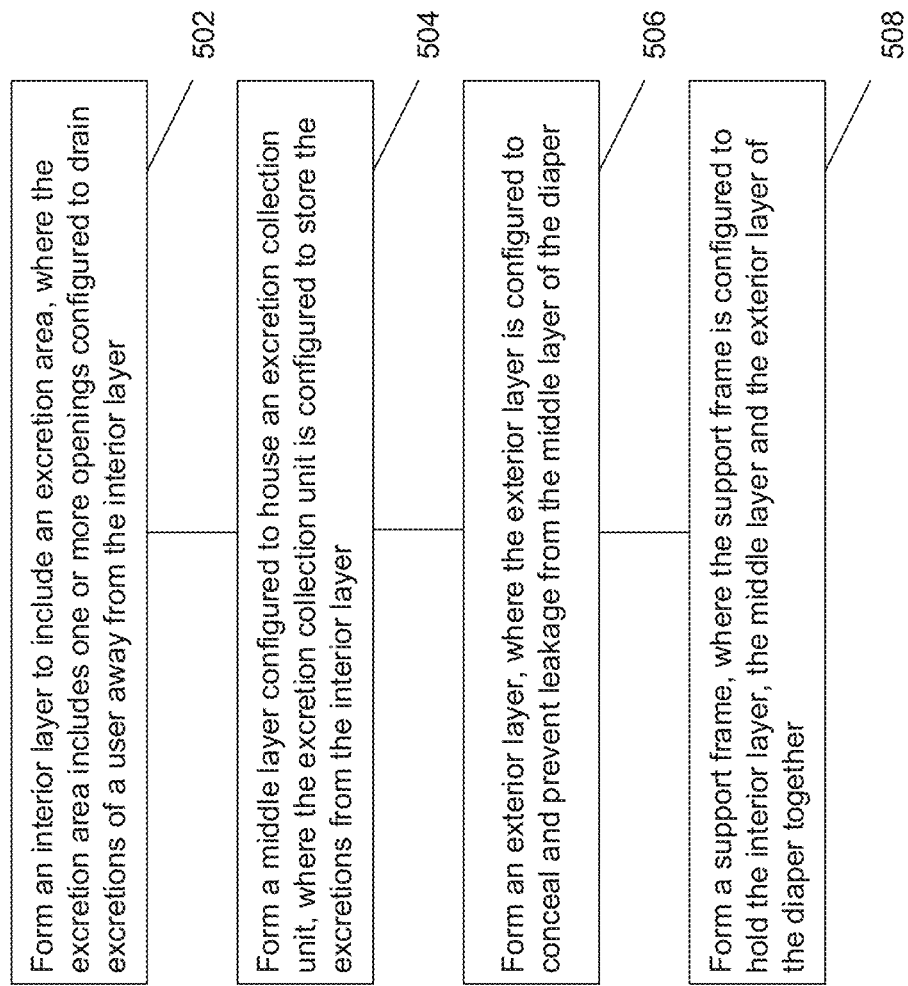
FIG. 5A illustrates an exemplary method of manufacturing a reusable diaper according to aspects of the present disclosure.

FIG. 5A illustrates an exemplary method of manufacturing a reusable diaper according to aspects of the present disclosure. As shown in FIG. 5A, in block 502, the method forms an interior layer to include an excretion area, where the excretion area includes one or more openings configured to drain excretions of a user away from the interior layer. The interior layer is formed using a hydrophobic material configured to repel the excretions of the user to the middle layer. In block 504, the method forms a middle layer configured to house an excretion collection unit, where the excretion collection unit is configured to store the excretions from the interior layer. In block 506, the method forms an exterior layer, where the exterior layer is configured to conceal and prevent leakage from the middle layer of the diaper. The exterior layer is formed using a breathable material to allow moisture from the middle layer to escape the diaper. In block 508, the method forms a support frame, where the support frame is configured to hold the interior layer, the middle layer and the exterior layer of the diaper together.

Figure 5B:
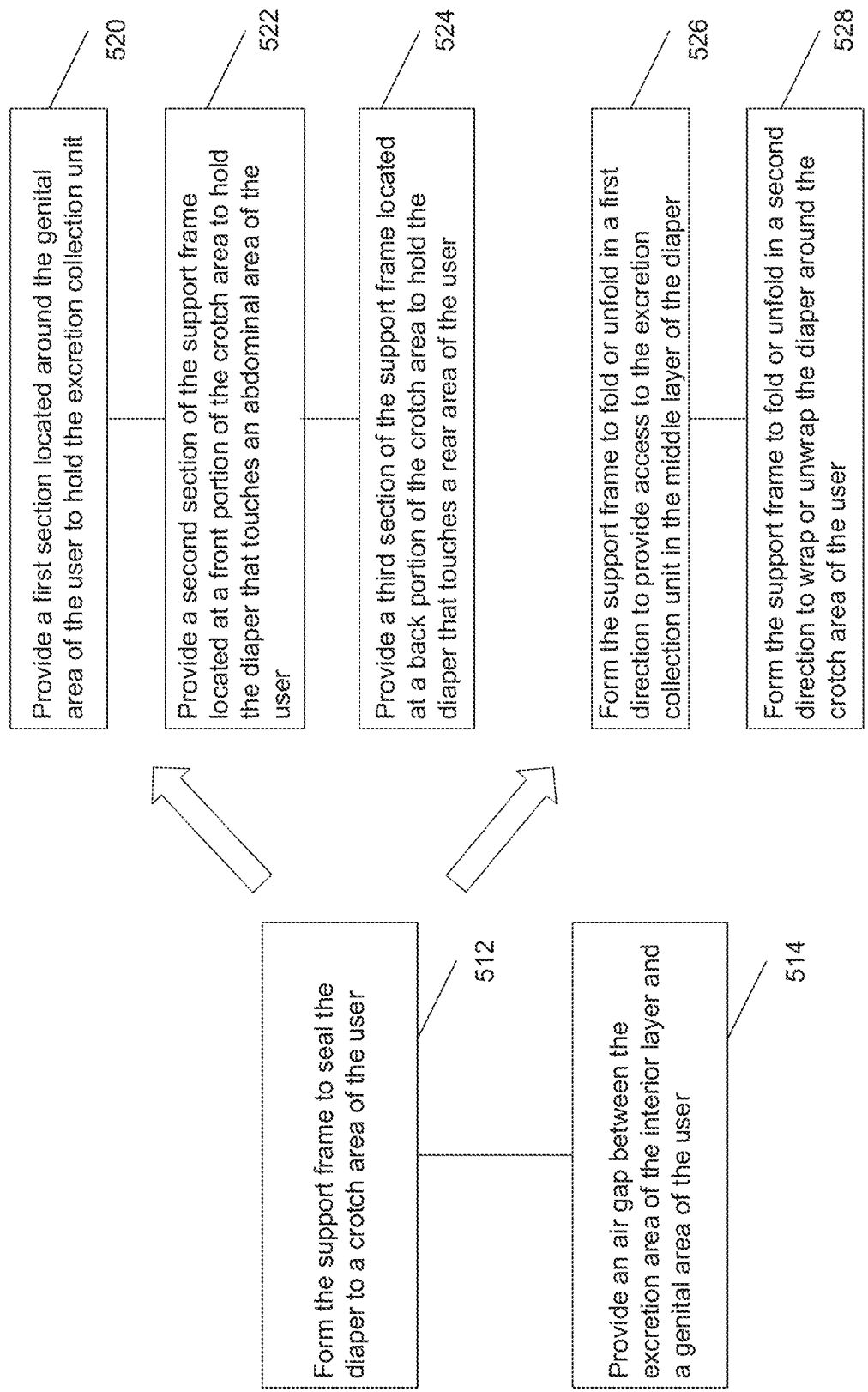
FIG. 5B illustrates an exemplary method of forming a support frame of the reusable diaper of FIG. 5A according to aspects of the present disclosure.

FIG. 5B illustrates an exemplary method of forming a support frame of the reusable diaper of FIG. 5A according to aspects of the present disclosure. In the example shown in FIG. 5B, in block 512, the method forms the support frame to seal the diaper to a crotch area of the user. In block 514, the method provides an air gap between the excretion area of the interior layer and a genital area of the user.

According to aspects of the present disclosure, the methods performed in block 512 may further include the methods performed in blocks 520, 522, and 524. In block 520, the method provides a first section located around the genital area of the user to hold the excretion collection unit. In block 522, the method provides a second section of the support frame located at a front portion of the crotch area to hold the diaper that touches an abdominal area of the user. In block 524, the method provides a third section of the support frame located at a back portion of the crotch area to hold the diaper that touches a rear area of the user. The support frame is made of polydimethylsiloxane rubber or thermoplastic elastomers, and is configured to wrap around the crotch area of the user to prevent leakage.

Moreover, the methods performed in block 512 may further include the methods performed in blocks 526 and 528. In block 526, the method forms the support frame to fold or unfold in a first direction to provide access to the excretion collection unit in the middle layer of the diaper. In block 528, the method forms the support frame to fold or unfold in a second direction to wrap or unwrap the diaper around the crotch area of the user.

Figure 5C:
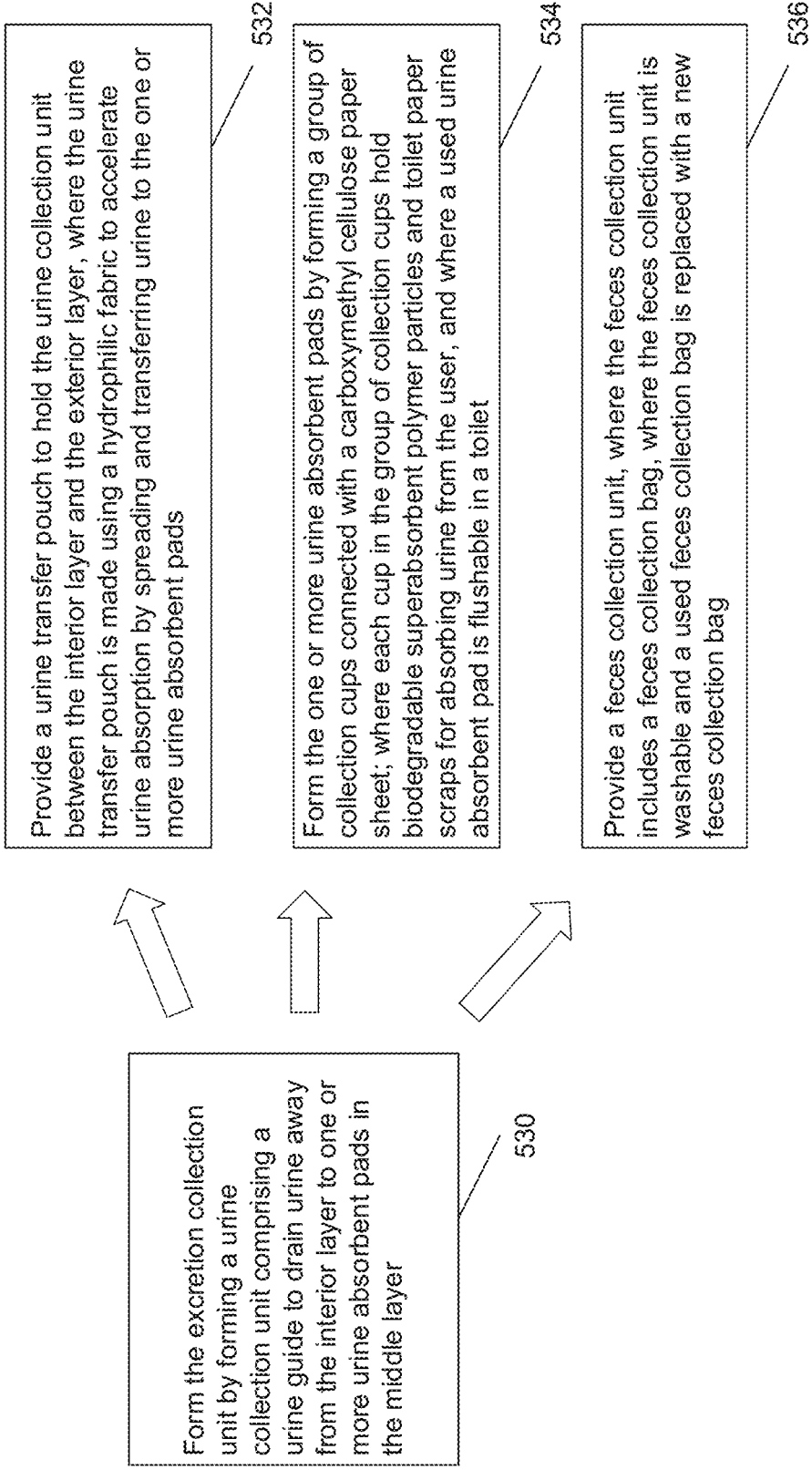
FIG. 5C illustrates an exemplary method of forming an excretion collection unit of the reusable diaper of FIG. 5A according to aspects of the present disclosure.

FIG. 5C illustrates an exemplary method of forming an excretion collection unit of the reusable diaper of FIG. 5A according to aspects of the present disclosure. In the exemplary method shown in FIG. 5C, in block 530, the method forms the excretion collection unit by forming a urine collection unit comprising a urine guide to drain urine away from the interior layer to one or more urine absorbent pads in the middle layer.

According to aspects of the present disclosure, the methods performed in block 530 may further include the methods performed in blocks 532, 534, and/or 536. In block 532, the method provides a urine transfer pouch to hold the urine collection unit between the interior layer and the exterior layer, where the urine transfer pouch is made using a hydrophilic fabric to accelerate urine absorption by spreading and transferring urine to the one or more urine absorbent pads. In block 534, the method forms the one or more urine absorbent pads by forming a group of collection cups connected with a carboxymethyl cellulose paper sheet; where each cup in the group of collection cups hold biodegradable superabsorbent polymer particles and toilet paper scraps for absorbing urine from the user, and where a used urine absorbent pad is flushable in a toilet. In block 536, the method provides a feces collection unit, where the feces collection unit includes a feces collection bag, where the feces collection unit is washable and a used feces collection bag is replaced with a new feces collection bag.

One skilled in the relevant art will recognize that many possible modifications and combinations of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the invention to the precise forms disclosed. Many modifications and variations are possible in view of the above teachings. The embodiments were chosen and described to explain the invention and their practical applications, and to enable others skilled in the art to best utilize the invention and various embodiments with various modifications as suited to the particular use contemplated.

What is claimed is:

1. A diaper, comprising:
   an interior layer that includes an excretion area, wherein the excretion area includes one or more openings configured to drain excretions of a user away from the interior layer;
   a middle layer comprising an excretion collection unit, wherein the excretion collection unit is configured to store the excretions from the interior layer,
   an exterior layer configured to conceal and prevent leakage from the middle layer of the diaper, and
   a support frame configured to hold the interior layer, the middle layer and the exterior layer of the diaper together.

2. The diaper of claim 1, wherein the interior layer is made of a hydrophobic material configured to repel the excretions of the user to the excretion collection unit in the middle layer.

3. The diaper of claim 1, wherein the support frame is further configured to seal the diaper to a crotch area of the user and to provide an air gap between the excretion area of the interior layer and a genital area of the user.

4. The diaper of claim 3, wherein the support frame further comprises:
   a first section located around the genital area of the user and configured to hold the excretion collection unit;
   a second section of the support frame that is configured to be located, when the diaper is applied to the user, at a front portion of the crotch area of the user and configured to hold a first portion of the diaper that touches an abdominal area of the user;
   a third section of the support frame that is configured to be located, when the diaper is applied to the user, at a back portion of the crotch area of the user and configured to hold a second portion of the diaper that touches a rear area of the user; and
   wherein the support frame is made of polydimethylsiloxane rubber or thermoplastic elastomers, and is configured to wrap around the crotch area of the user to prevent leakage.

5. The diaper of claim 3, wherein the support frame is configured to fold or unfold in a first direction to provide access to the excretion collection unit in the middle layer of the diaper, and wherein the support frame is further configured to fold or unfold in a second direction to wrap or unwrap the diaper around the crotch area of the user using a strapping mechanism that closes and opens the diaper to wrap and unwrap the diaper.

6. The diaper of claim 1, wherein the excretion collection unit comprises:
   a urine collection unit having a urine guide configured to drain urine away from the interior layer to one or more urine absorbent pads in the middle layer.

7. The diaper of claim 6, wherein the urine collection unit further comprises:
   a urine transfer pouch configured to hold the urine collection unit between the interior layer and the exterior layer, wherein the urine transfer pouch is made of a hydrophilic fabric and is configured to accelerate urine absorption by spreading and transferring urine to the one or more urine absorbent pads.

8. The diaper of claim 6, wherein the one or more urine absorbent pads comprises:
   a group of collection cups connected with a carboxymethyl cellulose paper sheet; wherein each cup in the group of collection cups is configured to hold biodegradable superabsorbent polymer particles and toilet paper scraps for absorbing urine from the user, and wherein the urine absorbent pad is flushable in a toilet after the diaper has been used to collect drained urine.

9. The diaper of claim 6, wherein the excretion collection unit further comprises:
   a feces collection unit, wherein the feces collection unit includes a feces collection bag, wherein the feces collection unit is washable and the feces collection bag is configured to be replaced with a new feces collection bag after the diaper has been used to collect feces.

10. The diaper of claim 1, wherein the exterior layer of the diaper comprises:
    a breathable material configured to allow moisture from the middle layer to escape the diaper.

11. A method of manufacturing a diaper, comprising:
    forming an interior layer that includes an excretion area, wherein the excretion area includes one or more openings configured to drain excretions of a user away from the interior layer;
    forming a middle layer comprising an excretion collection unit, wherein the excretion collection unit is configured to store the excretions from the interior layer;
    forming an exterior layer, wherein the exterior layer is configured to conceal and prevent leakage from the middle layer of the diaper; and
    forming a support frame, wherein the support frame is configured to hold the interior layer, the middle layer and the exterior layer of the diaper together.

12. The method of claim 11, further comprises:
    forming the interior layer using a hydrophobic material configured to repel the excretions of the user to the excretion collection unit in the middle layer.

13. The method of claim 11, further comprises:
    forming the support frame to seal the diaper to a crotch area of the user; and
    providing an air gap between the excretion area of the interior layer and a genital area of the user.

14. The method of claim 13, wherein forming the support frame further comprises:
    providing a first section located around the genital area of the user and configured to hold the excretion collection unit;
    providing a second section of the support frame that is configured to be located, when the diaper is applied to the user, at a front portion of the crotch area of the user and configured to hold a first portion of the diaper that touches an abdominal area of the user;

providing a third section of the support frame that is configured to be located, when the diaper is applied to the user, at a back portion of the crotch area of the user and configured to hold a second portion of the diaper that touches a rear area of the user; and wherein the support frame is made of polydimethylsiloxane rubber or thermoplastic elastomers, and is configured to wrap around the crotch area of the user to prevent leakage.

15. The method of claim 13, further comprises:

forming the support frame to fold or unfold in a first direction to provide access to the excretion collection unit in the middle layer of the diaper, and forming the support frame to fold or unfold in a second direction to wrap or unwrap the diaper around the crotch area of the user using a strapping mechanism that closes and opens the diaper to wrap and unwrap the diaper.

16. The method of claim 11, further comprises:

forming the excretion collection unit by forming a urine collection unit comprising a urine guide to drain urine away from the interior layer to one or more urine absorbent pads in the middle layer.

17. The method of claim 16, wherein forming the urine collection unit further comprises:

providing a urine transfer pouch to hold the urine collection unit between the interior layer and the exterior layer, wherein the urine transfer pouch is made using a hydrophilic fabric to accelerate urine absorption by spreading and transferring urine to the one or more urine absorbent pads.

18. The method of claim 16, further comprises:

forming the one or more urine absorbent pads by forming a group of collection cups connected with a carboxymethyl cellulose paper sheet; wherein each cup in the group of collection cups hold biodegradable superabsorbent polymer particles and toilet paper scraps for absorbing urine from the user, and wherein the urine absorbent pad is flushable in a toilet after the diaper has been used to collect drained urine.

19. The method of claim 16, wherein forming the excretion collection unit further comprises:

providing a feces collection unit, wherein the feces collection unit includes a feces collection bag, wherein the feces collection unit is washable and the feces collection bag is configured to be replaced with a new feces collection bag after the diaper has been used to collect feces.

20. The method of claim 11, further comprises:

forming the exterior layer of the diaper using a breathable material to allow moisture from the middle layer to escape the diaper.

* * * * *